US010724969B2

(12) United States Patent
Xing et al.

(10) Patent No.: US 10,724,969 B2
(45) Date of Patent: Jul. 28, 2020

(54) X-RAY DETECTION METHOD AND X-RAY DETECTOR

(71) Applicants:Tsinghua University, Beijing (CN); Nuctech Company Limited, Beijing (CN)

(72) Inventors: Yuxiang Xing, Beijing (CN); Xiaoyue Guo, Beijing (CN); Zhi Deng, Beijing (CN); Le Shen, Beijing (CN); Li Zhang, Beijing (CN); Zhiqiang Chen, Beijing (CN); Liang Li, Beijing (CN)

(73) Assignees: NUCTECH COMPANY LIMITED, Beijing (CN); TSINGHUA UNIVERSITY, Beijing (CN)

( * ) Notice: Subject to any disclaimer, the term of this patent is extended or adjusted under 35 U.S.C. 154(b) by 123 days.

(21) Appl. No.: 16/175,796

(22) Filed: Oct. 30, 2018

(65) Prior Publication Data

US 2019/0086562 A1 Mar. 21, 2019

Related U.S. Application Data

(63) Continuation of application No. PCT/CN2017/072832, filed on Feb. 3, 2017.

(30) Foreign Application Priority Data

May 5, 2016 (CN) .......................... 2016 1 0294662

(51) Int. Cl.
*G01N 23/04* (2018.01)
*A61B 6/00* (2006.01)
(Continued)

(52) U.S. Cl.
CPC ........... *G01N 23/04* (2013.01); *A61B 6/5205* (2013.01); *A61B 6/032* (2013.01); *A61B 6/4241* (2013.01);
(Continued)

(58) Field of Classification Search
CPC ................. G01N 23/04; G01N 23/046; G01N 2223/419; G01N 2223/423; A61B 6/5205; A61B 6/482; A61B 6/4241; A61B 6/032
See application file for complete search history.

(56) References Cited

U.S. PATENT DOCUMENTS

| 6,373,919 B1 * | 4/2002 | Horiuchi ................ A61B 6/032 378/4 |
| 2006/0109949 A1 * | 5/2006 | Tkaczyk ................ A61B 6/032 378/4 |

(Continued)

FOREIGN PATENT DOCUMENTS

| CN | 1880949 A | 12/2006 |
| CN | 101313332 A | 11/2008 |

(Continued)

OTHER PUBLICATIONS

Wikipedia, "Matrix representation", (Mar. 23, 2015), obtained from the Internet at <<https://web.archive.org/web/20150323040716/https://en.wikipedia.org/wiki/Matrix_representation>>. (Year: 2015).*

(Continued)

*Primary Examiner* — Chih-Cheng Kao
(74) *Attorney, Agent, or Firm* — Schwegman Lundberg & Woessner, P.A.

(57) ABSTRACT

An X-ray detection method and an X-ray detector are provided. The X-ray detection method according to embodiments of the present disclosure includes: dividing an energy range of photons emitted by an X-ray source into a number N of energy windows, where N is an integer greater than 0; obtaining a weighting factor for each of the number N of energy windows based on linear attenuation coefficients of a substance of interest and a background substance of an imaging target; obtaining a weighting factor matrix for M output channels of an X-ray detector based on the weighting factor for each of the number N of energy windows, where (Continued)

M is an integer greater than 0; and obtaining output results of the M output channels based on the weighting factor matrix and numbers of photons having an energy range falling into individual energy windows of the number N of energy windows.

7 Claims, 4 Drawing Sheets

(51) Int. Cl.
  *G01N 23/046* (2018.01)
  *A61B 6/03* (2006.01)
(52) U.S. Cl.
  CPC ............ *A61B 6/482* (2013.01); *G01N 23/046* (2013.01); *G01N 2223/419* (2013.01); *G01N 2223/423* (2013.01)

(56) References Cited

U.S. PATENT DOCUMENTS

| 2006/0284098 | A1  |        | 12/2006 | Vija      |          |
|--------------|-----|--------|---------|-----------|----------|
| 2008/0013673 | A1* |        | 1/2008  | Ruhmschopf | A61B 6/482 |
|              |     |        |         |           | 378/7    |
| 2014/0233694 | A1  |        | 8/2014  | Wang et al. |        |

FOREIGN PATENT DOCUMENTS

| CN | 103472074   A  | 12/2013 |
| CN | 104215997   A  | 12/2014 |
| CN | 104422704   A  | 3/2015  |
| CN | 104995690   A  | 10/2015 |
| CN | 105092617   A  | 11/2015 |
| CN | 105510364   A  | 4/2016  |
| JP | H385482        | 4/1991  |
| JP | 2002524126     | 8/2002  |
| JP | 2004512512  A  | 4/2004  |
| JP | 2006101926  A  | 4/2006  |
| JP | 2010082031  A  | 4/2010  |
| JP | 2011503570  A  | 1/2011  |
| JP | 2014158713  A  | 9/2014  |
| JP | 2015200649  A  | 11/2015 |
| WO | 2014176328  A1 | 10/2014 |

OTHER PUBLICATIONS

"Chinese Application No. 201610294662.3, First Office Action dated Jun. 21, 2019", (Jun. 21, 2019), 16 pgs.

"Japanese Application No. 2018-545666, Notice of Reasons for Refusal dated Jul. 19, 2019", (Jul. 19, 2019), 6 pgs.

"European Application No. 17792367.9, Extended European Search Report dated Jan. 16, 2020", (Jan. 16, 2020), 8 pgs.

Endrizzi, M., et al., "Multi-energy computer tomography using pre-reconstruction decomposition and iterative reconstruction algorithms", J. Phys. D: Appl. Phys. 45(47) (2012), IOP Publishing Ltd., (Nov. 1, 2012), 1-8.

Rakvongthai, Yothin, et al., "Spectral CT Using Multiple Balanced K-Edge Filters", IEEE Transactions on Medical imaging, IEEE Service Center, Piscataway, NJ, US, vol. 34, No. 3, (Mar. 1, 2015), 740-747.

Schmidt, Taly Gilat, "Optimal "image-based" weighting for energy-resolved CT", Medical Physics, AIP, Melville, NY, US, vol. 36, No. 7, (Jun. 10, 2009), 3018-3027.

* cited by examiner

X-RAY DETECTION METHOD AND X-RAY DETECTOR

CROSS-REFERENCE TO RELATED APPLICATION

This application is a continuation of International Application No. PCT/CN2017/072832, filed on Feb. 3, 2017, which claims priority to Chinese Patent Application No. 201610294662.3, filed on May 5, 2016, both of which are hereby incorporated by reference in their entireties.

FIELD

The present disclosure generally relates to a technical field of X-ray imaging, and more particularly relates to an X-ray detection method and an X-ray detector.

BACKGROUND

Since the discovery of X-rays by Roentgen, X-ray based CT imaging technology has developed rapidly and is widely used in medical imaging and security inspection. At present, detectors applied for X-ray imaging mainly employ the following two methods for signal acquisition: energy integration and photon counting. In recent years, due to advantages of multi-spectral imaging in discrimination of material compositions or the like, a photon counting detector has become a research hotspot in related fields. There are several research institutes and companies in the world dedicated to research and production of photon counting detectors for X-ray imaging. The photon counting detector counts photons with distinct energy according to the energy of the individual photons passing through an object. In this way, low-energy photons can be filtered out by setting a threshold to reduce noise and radiation. At the same time, by setting a plurality of thresholds, the counting for X-rays with a wide energy spectrum distribution can be performed per energy regions, and imaging results of different energy regions can be directly obtained. Compared with an energy integration detector, the photon counting detector can eliminate influence of low-energy noise on the imaging and improve image quality. On the other hand, the photon counting detector can distinguish the energy more precisely and reduce correlation among data acquired for X-ray imaging. Thus, the X-ray imaging by the photon counting detector can improve accuracy of material discrimination, precision of component quantization, and the like.

The photon counting detector plays an increasingly important role in the X-ray imaging. However, it has a high cost. On the other hand, the photon counting detector is greatly limited by the counting rate and the number of energy window channels, and accordingly it is hard to optimize efficiency of data acquisition. In an ideal case, X-ray photons of different energy carry different information. If different photons can be subdivided referring to sufficient energy intervals and processed differently according to their individual energy, the image quality can be optimized to the greatest extent. The above two signal acquisition methods applied to X-ray imaging detectors correspond to two "energy-weighted" signal processing methods: the energy integration detector uses energy as a weight to perform a weighted accumulation of all photon signals to obtain an output; the photon counting detector performs a weighted accumulation of the individual photons with a constant as a weight in a specified energy range to obtain an output. No signal optimization strategy can be used for the output of each of these two detectors. Thus the image quality of CT imaging systems based on them is necessarily limited.

SUMMARY

In view of the above problems, a novel X-ray detection method and a novel X-ray detector are provided in the present disclosure.

An X-ray detection method according to embodiments of the present disclosure includes: dividing an energy range of photons emitted by an X-ray source into a number N of energy windows, where N is an integer greater than 0; obtaining a weighting factor for each of the number N of energy windows based on linear attenuation coefficients of a substance of interest and a background substance of an imaging target; obtaining a weighting factor matrix for M output channels of an X-ray detector based on the weighting factor for each of the number N of energy windows, where M is an integer greater than 0; and obtaining output results of the M output channels based on the weighting factor matrix and numbers of photons having an energy range falling into individual energy windows of the number N of energy windows.

An X-ray detector according to embodiments of the present disclosure includes: N energy window discriminators, each of which counts a number of photons that are emitted by an X-ray source and have an energy range falling into a discrimination range of the energy window discriminator; N sets of multipliers, each of which includes M multipliers, wherein a k-th multiplier in an i-th set of multipliers is configured to multiply the number of photons counted by an i-th energy window discriminator of the N energy window discriminators by a weighting factor at a k-th row and an i-th column of an M×N weighting factor matrix, where M, N, k and i are all integers greater than 0; and M adders, wherein a k-th adder of the M adders is configured to accumulate products obtained at the k-th multipliers of individual sets of multipliers so as to obtain an output result of a k-th output channel of M output channels of the X-ray detector, wherein the weighting factor matrix is obtained based on linear attenuation coefficients of a substance of interest and a background substance of an imaging target.

With the X-ray detection method and the X-ray detector according to embodiments of the present disclosure, signals for a plurality of energy windows can be obtained flexibly; the number of output channels for the X-ray detector can be reduced; the bit rate of the output data can be reduced; and thus it is possible to realize a spectral CT signal acquisition of higher efficiency.

BRIEF DESCRIPTION OF THE DRAWINGS

The present disclosure may be better understood from the following description of the embodiments of the present disclosure, in which.

DETAILED DESCRIPTION

Features and exemplary embodiments of various aspects of the present disclosure will be described in detail below. In the following detailed description, numerous specific details are set forth so as to provide a comprehensive understanding of the present disclosure. It will be apparent to those skilled in the art, however, that the present application may be practiced without some of these specific details. The following description of the embodiments is merely given by way of examples to provide a better understanding of the present disclosure. The present disclosure is in no way limited to any specific configurations and algorithms set forth below, but is attempted to cover any modification, replacement or improvement of elements, components or algorithms without departing from the spirit and scope of the present disclosure. In the drawings and the following description, well-known structures and techniques are not shown in order to avoid unnecessarily obscuring the disclosure.

In view of the above described problems, a novel X-ray detection method and a novel X-ray detector are proposed in the present disclosure. The X-ray detection method and the X-ray detector according to embodiments of the present disclosure will be described in detail below with reference to the accompanying drawings.

Figure 1:
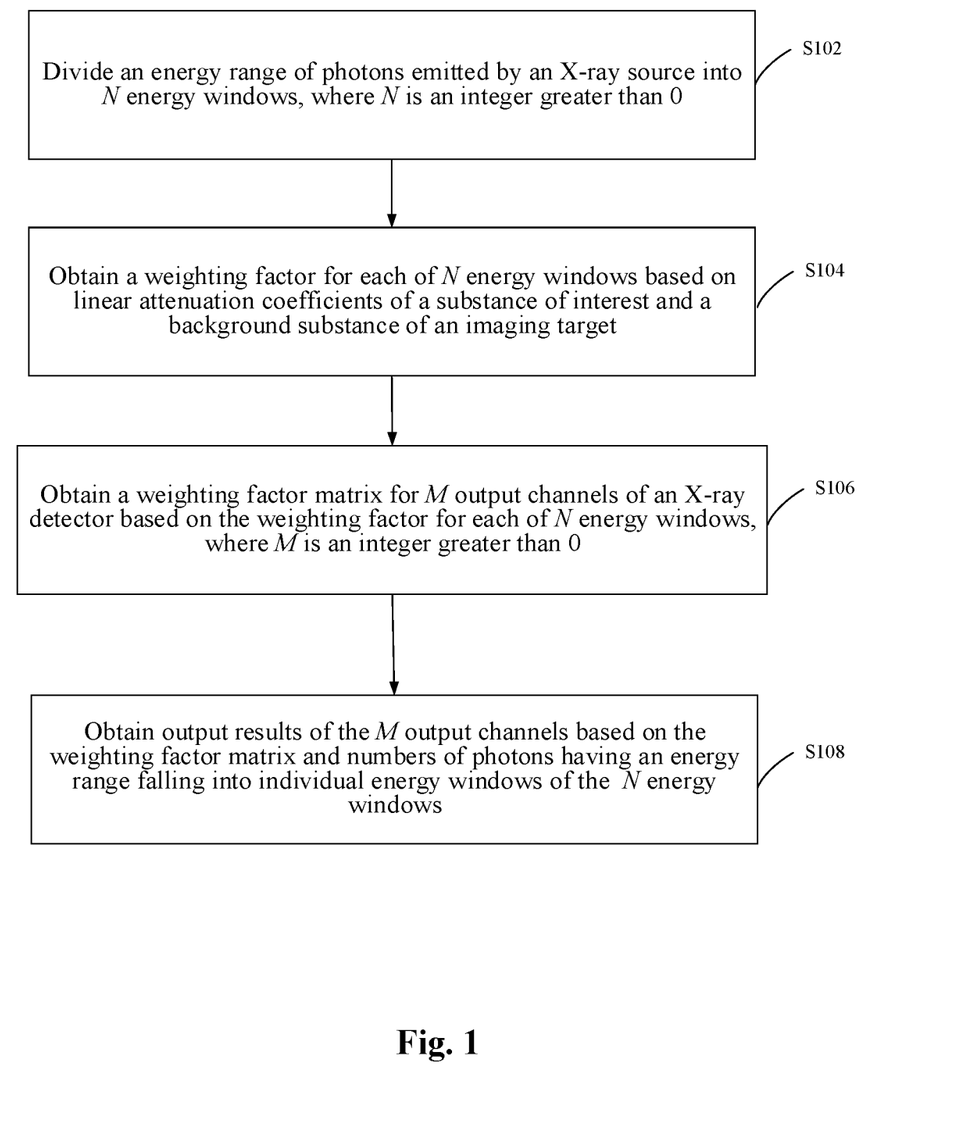
FIG. 1 is a flow chart of an X-ray detection method according to embodiments of the present disclosure.

FIG. 1 is a flow chart of an X-ray detection method according to embodiments of the present disclosure. As shown in FIG. 1, the X-ray detection method may include the following steps.

At S102, an energy range of photons emitted by an X-ray source may be divided into a number N of energy windows, where N is an integer greater than 0. The energy range of the photons emitted by the X-ray source may be $E_{min}<E<E_{max}$, and boundaries of the number N of energy windows may be $[E_0, E_n]$, where $E_{min} \leq E_0 < E_n \leq E_{max}$. These energy windows may be obtained by an equal interval division or an unequal interval division.

At S104, a weighting factor for each of the number N of energy windows may be obtained based on linear attenuation coefficients of a substance of interest and a background substance of an imaging target. Here, the substance of interest and the background substance of the imaging target may be specified according to imaging requirements. For example, the imaging target is a concentration of an iodine contrast agent, iodine may be selected as the substance of interest, and water may be selected as the background substance. The weighting factor for each energy window can be obtained in any of the following three ways.

a) Suppose that the linear attenuation coefficient of the substance of interest is $\mu_1(E)$, and the linear attenuation coefficient of the background substance is $\mu_2(E)$. With respect to an i-th energy window $[E_i, E_{i+1}]$ among the number N of energy windows (here, i is any integer greater than 0), the weighting factor $\omega_i$ for the i-th energy window can be calculated as follows:

$$\omega_i = \alpha \int_{E_i}^{E_{i+1}} \mu_1(E)dE + (1-\alpha) \int_{E_i}^{E_{i+1}} \mu_1(E)dE, \; 0 \leq \alpha \leq 1,$$

where the $\alpha$ has no physical meaning and may be any number between 0 and 1.

In other words, the linear attenuation coefficient of the substance of interest and the linear attenuation coefficient of the background substance may be integrated respectively within an energy range of the i-th energy window, and then the weighting factor for the i-th energy window can be calculated by carrying out an addition operation with the integration result of the linear attenuation coefficient of the substance of interest and the integration result of the linear attenuation coefficient of the background substance.

b) Suppose that the linear attenuation coefficient of the substance of interest is $\mu_1(E)$, the linear attenuation coefficient of the background substance is $\mu_2(E)$, an average or typical thickness of the substance of interest penetrated by the X-rays emitted by the X-ray source is $d_1$, and an average or typical thickness of the background substance penetrated by the X-rays emitted by the X-ray source is $d_2$. With respect to an i-th energy window $[E_i, E_{i+1}]$ among the number N of energy windows (here, i is any integer greater than 0), the weighting factor $\omega_i$ for the i-th energy window can be calculated as follows:

$$\omega_i = \frac{T_{1i} - T_{2i}}{T_{1i} + T_{2i}},$$

where $$T_{1i} = \frac{\int_{E_i}^{E_{i+1}} \Phi_i(E) T_1(E) dE}{\langle n_{1i} \rangle}, \; T_1(E) = e^{-\mu_1(E)d_1}, \; \langle n_{1i} \rangle = \int_{E_i}^{E_{i+1}} \Phi_i(E)dE;$$

$$T_{2i} = \frac{\int_{E_i}^{E_{i+1}} \Phi_i(E) T_2(E) dE}{\langle n_{2i} \rangle}, \; T_2(E) = e^{-\mu_2(E)d_2}, \; \langle n_{2i} \rangle = \int_{E_i}^{E_{i+1}} \Phi_i(E)dE;$$

and $\Phi_i(E)$ is an energy spectrum of the X-rays emitted by the X-ray source.

c) Suppose that the linear attenuation coefficient of the substance of interest is $\mu_1(E)$, the linear attenuation coefficient of the background substance is $\mu_2(E)$, an average or typical thickness of the substance of interest penetrated by the X-rays emitted by the X-ray source is $d_1$, and an average or typical thickness of the background substance penetrated by the X-rays emitted by the X-ray source is $d_2$. With respect to an i-th energy window $[E_i, E_{i+1}]$ among the number N of energy windows (here, i is any integer greater than 0), given $E_i = e_i$ and $E_{i+1} = e_{i+p}$, that is, the i-th energy window $[E_i, E_{i+1}]$ includes p+1 energy points respectively corresponding to an energy spectrum $\Phi_i(e_j)$, where j=0, 1, . . . , p, then the weighting factor $\omega_i$ for the i-th energy window can be calculated as follows:

$$\omega_i = \alpha \frac{L_0 + 2\sum_{j=1}^{j=p-1} L_j + L_p}{G_0 + 2\sum_{j=1}^{j=p-1} G_j + G_p},$$

where $\alpha$ is any constant, $L_j = L(e_j) = \Phi_i(e_j)(e^{-x1j} - e^{-x2j}), j=0,1,\ldots,p,$ $G_j = G(e_j) = \Phi_i(e_j)(e^{-x1j} + e^{-x2j}), j=0,1,\ldots,p,$ $x_{1j} = x_1(e_j) = \mu_1(e_j)d_1, x_{2j} = x_2(e_2) = \mu_2(e_j)d_2, j=0,1,\ldots,p.$ As described above, in the ways b) and c) of obtaining the weighting factor for each energy window, the weighting factor for the i-th energy window is calculated based on the linear attenuation coefficient of the substance of interest, the linear attenuation coefficient of the background substance, the energy spectrum of the X-rays emitted by the X-ray source in the i-th energy window, the average thickness of the substance of interest penetrated by the X-rays emitted by the X-ray source, and the average thickness of the background substance penetrated by the X-rays emitted by the X-ray source.

At S106, a weighting factor matrix (hereinafter referred to as the weighting factor matrix A for convenience) for M output channels of the X-ray detector may be obtained based on the weighting factor for each of the number N of energy windows, where M is an integer greater than 0.

In some embodiments, for the k-th output channel of the X-ray detector (k is any integer greater than 0 and less than M), if the i-th energy window of the number N of energy windows belongs to the k-th output channel, that is, if the i-th energy window belongs to a set $\Omega_k$ of energy windows corresponding to the k-th output channel, then a weighting factor $a_{k,i}$ corresponding to the i-th energy window and the k-th output channel in the weight factor matrix A can be calculated by normalizing the weighting factor $\omega_i$ for the i-th energy window according to the following equation.

$$a_{k,i} = \frac{\mathrm{round}\left(\frac{\omega_i}{\omega_i^{max}} \cdot 2^B\right)}{2^B}$$

Here, $\omega_i^{max}$ is the largest weighting factor for the set $\Omega_k$ of energy windows corresponding to the k-th output channel, round(•) represents a rounding function, and B represents a number of bits indicating a precision of quantizing the $\omega_i$.

If the i-th energy window does not belong to the k-th output channel, that is, if the i-th energy window does not belong to the set $\Omega^k$ of energy windows corresponding to the k-th output channel, then the weighting factor $a_{k,i}$ corresponding to the i-th energy window and the k-th output channel in the weight factor matrix A can be set to 0.

At S108, the output results of the M output channels of the X-ray detector may be obtained based on the weighting factor matrix A and the numbers of photons having an energy range falling into individual energy windows of the number N of energy windows.

In some embodiments, the output results of the M output channels can be obtained by multiplying the weighting factor matrix A by a column vector x consisting of the numbers of photons having the energy range falling into individual energy windows of the number N of energy windows. The column vector x and the weighting factor matrix A are given below, and the output results of the M output channels are y=Ax.

$$x = \begin{pmatrix} x_1 \\ x_2 \\ \vdots \\ x_N \end{pmatrix}$$

$$A = \begin{pmatrix} a_{11} & a_{12} & \cdots & a_{1N} \\ a_{21} & a_{22} & \cdots & a_{2N} \\ \vdots & \vdots & \ddots & \vdots \\ a_{M1} & a_{M2} & \cdots & a_{MN} \end{pmatrix}$$

Figure 2:
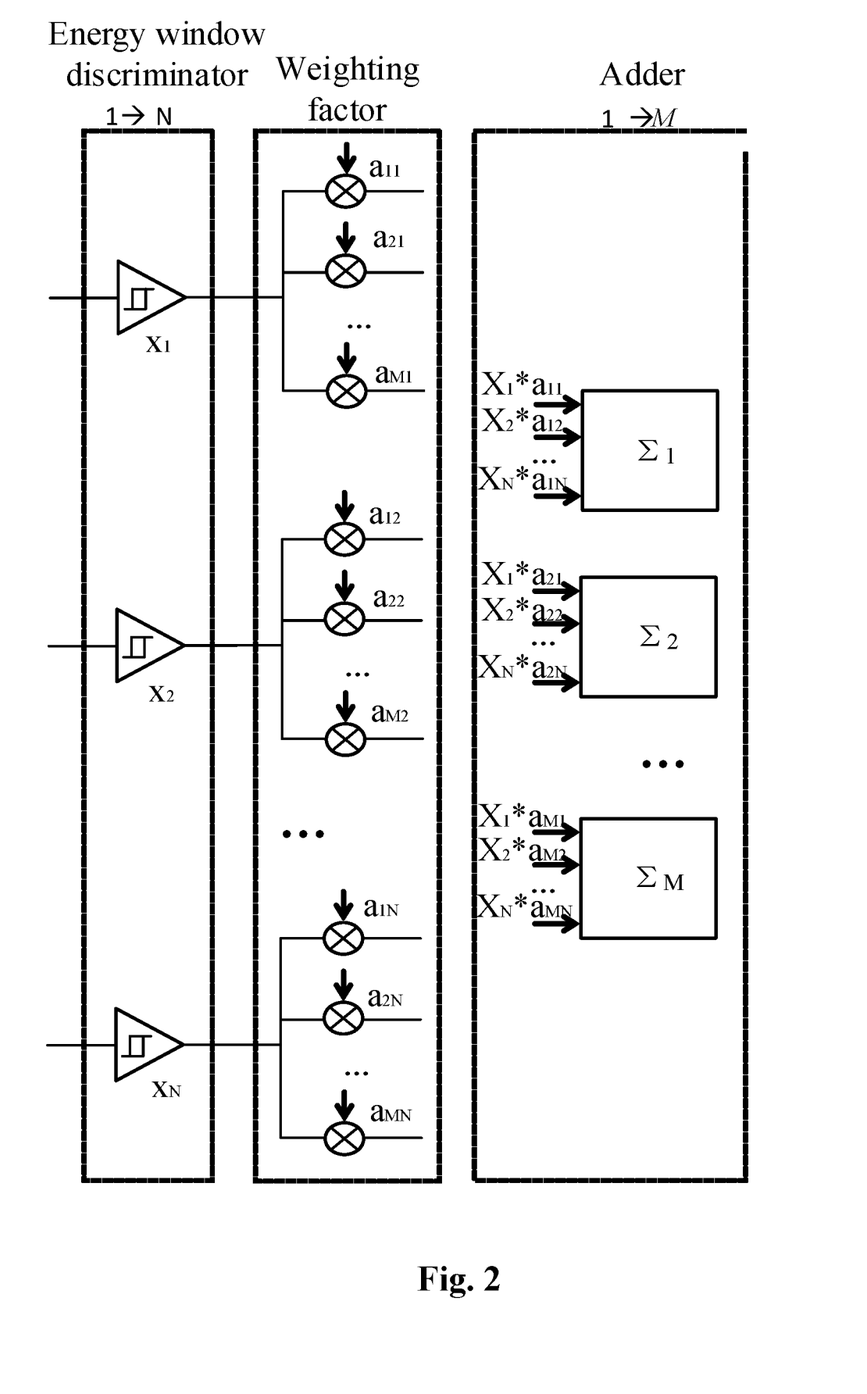
FIG. 2 is a schematic structural diagram of an X-ray detector according to embodiments of the present disclosure.

FIG. 2 is a schematic structural diagram of an X-ray detector according to embodiments of the present disclosure. The X-ray detector is designed based on the above described X-ray detection method. As shown in FIG. 2, the X-ray detector may include: N energy window discriminators, each of which counts a number of photons that are emitted by an X-ray source and have an energy range falling into a discrimination range of the energy window discriminator (each energy window discriminator corresponds to an energy window of the above N energy windows); N sets of multipliers, each of which includes M multipliers, wherein a k-th multiplier in an i-th set of multipliers is configured to multiply the number of photons counted by an i-th energy window discriminator of the N energy window discriminators by a weighting factor at a k-th row and an i-th column of an M×N weighting factor matrix (i.e. the above weighting factor matrix A); and M adders, wherein a k-th adder is configured to accumulate products obtained at the k-th multipliers of individual sets of multipliers so as to obtain an output result of a k-th output channel of M output channels of the X-ray detector.

In some embodiments, the X-ray detector of FIG. 2 may further include a matrix obtaining unit. The matrix obtaining unit may be configured to perform calculations for any energy window of the N energy windows according to the above described methods. For example, the weighting factor $\omega_i$ for the i-th energy window and the weighting factor $a_{k,i}$ corresponding to the i-th energy window and the k-th output channel in the weighting factor matrix A may be calculated.

The existing photon counting detector outputs the output results of all output channels. If there are 128 output channels, 128 results will be output, and then the 128 results will be used for weighting or other operations. The X-ray detection method and the X-ray detector according to embodiments of the present disclosure can flexibly set the number of output channels according to actual needs, so that the bandwidth for data transmission can be saved. Here, since the weighting factor is programmable, it is flexible and convenient to use.

Examples of applying the above-described X-ray detection method and the X-ray detector for X-ray imaging are given below.

It is assumed that the energy range of the photons emitted by the X-ray source is from 21 kV to 51 kV (i.e., [21, 51]), and the corresponding energy spectrum is $\Phi(E)$ (i.e., the number of photons corresponding to each energy point is $\Phi(E)$). The energy range is divided into seven energy windows, that is, N=7.

The X-ray detector is provided with 7 output channels, that is, M=7, and the sets of energy windows corresponding to individual output channels are:

| K | 1 | 2 | 3 | 4 | 5 | 6 | 7 |
|---|---|---|---|---|---|---|---|
| $\Omega_k$/kV | [21, 22] | [22, 27] | [27, 32] | [32, 37] | [37, 42] | [42, 47] | [47, 51] |

The linear attenuation coefficient of the substance of interest (i.e., Material 1) is $\mu_1(E)$, the linear attenuation coefficient of the background substance (i.e., Material 2) is $\mu_2(E)$, the average or typical thickness of the Material 1 penetrated by the X-rays emitted by the X-ray source is $d_1$ cm, and the average or typical thickness of the Material 2 penetrated by the X-rays emitted by the X-ray source is $d_2$ cm.

Material 2 is a cylinder having a filling radius of 2 cm and a thickness of 2.5 cm; Material 1 contains three cylinders having a filling radius of 0.5 cm and a thickness of 2 cm, 1.5 cm, and 1 cm, respectively.

The i-th energy window among the above 7 energy windows is $[E_i, E_{i+1}]$, $E_i=e_i$kV and $E_{i+1}=e_{i+1}$kV, that is, the i-th energy window includes two energy points respectively corresponding to an energy spectrum $\Phi_i(e_j)$, where j=0, 1, and the weighting factor $\omega_i$ for the i-th energy window can be calculated as follows:

$$\omega_i = \alpha \frac{L_0 + L_1}{G_0 + G_1},$$

where given $\alpha=1$ $L_j=L(e_j)=\Phi_i(e_j)(e^{-x1j}-e^{-x2j}), j=0,1,$ $G_j=G(e_j)=\Phi_i(e_j)(e^{-x1j}+e^{-x2j}), j=0,1,$ $x_{1j}=x_1(e_j)=\mu_1(e_j)d_1, x_{2j}=x_2(e_2)=\mu_2(e_j)d_2, j=0,1.$ After normalizing each $\omega_i$ (i=1, 2, ..., 7), the $a_{k,i}$ can be obtained:

$$a_{k,i} = \frac{\text{round}\left(\frac{\omega_i}{\omega_i^{max}} \times 2^4\right)}{2^4}.$$

An image is reconstructed using a method of Filtered Back Projection. A quantitative comparison in terms of signal-to-noise ratios is made below between a CT reconstructed image (a weighted reconstructed image) obtained by using the X-ray detector according to embodiments of the present disclosure and a CT reconstructed image (an unweighted reconstructed image) obtained by using a photon counting detector having a constant weight of 1.

Example 1

Firstly, the substance of interest (Material 1) is selected as a breast tissue, and the background material (Material 2) is water. Secondly, in the selected energy range of 21 kV to 51 kV, the energy windows corresponding to individual output channels are fixed: channel 1 corresponds to the energy window [21, 22], channel 2 corresponds to the energy window [22, 27], channel 3 corresponds to the energy window [27, 32], channel 4 corresponds to the energy window [32, 37], channel 5 corresponds to the energy window [37, 42], channel 6 corresponds to the energy window [42, 47], and channel 7 corresponds to the energy window [47, 51].

Therefore, the weights corresponding to the individual channels are: channel 1 corresponds to the weight of 1, channel 2 corresponds to the weight of 0.75, channel 3 corresponds to the weight of 0.6875, channel 4 corresponds to the weight of 0.5, channel 5 corresponds to the weight of 0.5, channel 6 corresponds to the weight of 0.4375, and channel 7 corresponds to the weight of 0.4375.

Figure 3A:
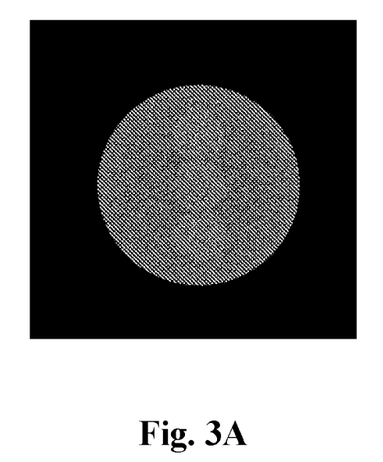
FIG. 3A and FIG. 3B respectively shows a CT image obtained by using a photon counting detector and a CT image obtained by using an X-ray detector according to embodiments of the present disclosure.
Figure 3B:
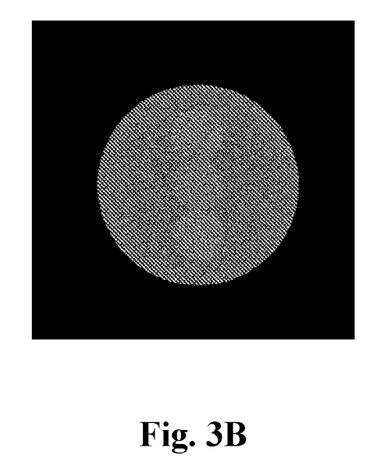

The signal-to-noise ratio of the substance of interest and the background substance in the reconstructed image obtained by using the photon counting detector and the signal-to-noise ratio of the substance of interest and the background substance in the reconstructed image obtained by using the X-ray detector according to embodiments of the present disclosure are respectively calculated as: the signal-to-noise ratio of the reconstructed image obtained by using the photon counting detector is 202.57, and the signal-to-noise ratio of the reconstructed image obtained by using the X-ray detector according to embodiments of the present disclosure is 207.75. FIG. 3A and FIG. 3B show a CT image obtained by using the photon counting detector and a CT image obtained by using the X-ray detector according to embodiments of the present disclosure, respectively.

Example 2

Firstly, the substance of interest (Material 1) is selected as a breast tissue, and the background material (Material 2) is fat. Secondly, in the selected energy range of 21 kV to 51 kV, the energy windows corresponding to individual output channels are fixed: channel 1 corresponds to the energy window [21, 22], channel 2 corresponds to the energy window [22, 27], channel 3 corresponds to the energy window [27, 32], channel 4 corresponds to the energy window [32, 37], channel 5 corresponds to the energy window [37, 42], channel 6 corresponds to the energy window [42, 47], and channel 7 corresponds to the energy window [47, 51].

Therefore, the weights corresponding to the individual channels are: channel 1 corresponds to the weight of 1, channel 2 corresponds to the weight of 0.75, channel 3 corresponds to the weight of 0.625, channel 4 corresponds to the weight of 0.5, channel 5 corresponds to the weight of 0.4375, channel 6 corresponds to the weight of 0.4375, and channel 7 corresponds to the weight of 0.375.

Figure 4A:
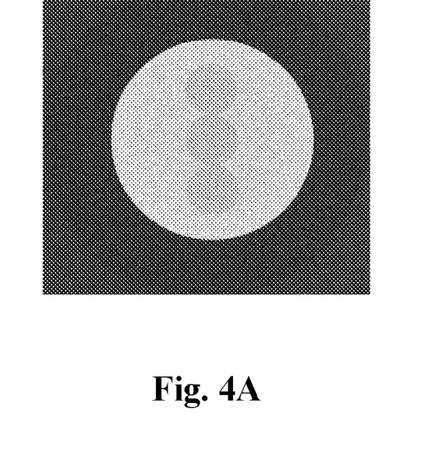
FIG. 4A and FIG. 4B respectively shows a CT image obtained by using a photon counting detector and a CT image obtained by using an X-ray detector according to embodiments of the present disclosure.
Figure 4B:
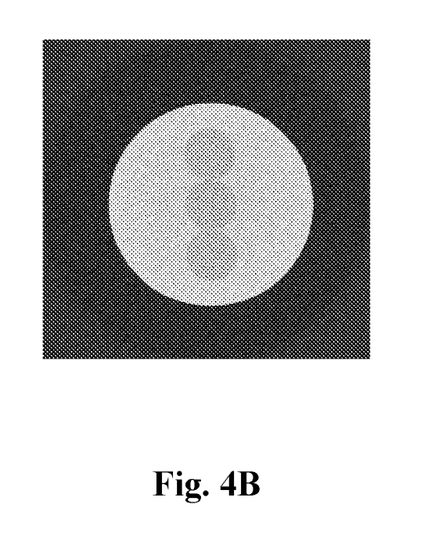

The signal-to-noise ratio of the substance of interest and the background substance in the reconstructed image obtained by using the photon counting detector and the signal-to-noise ratio of the substance of interest and the background substance in the reconstructed image obtained by using the X-ray detector according to embodiments of the present disclosure are respectively calculated as: the signal-to-noise ratio of the reconstructed image obtained by using the photon counting detector is 219.85, and the signal-to-noise ratio of the reconstructed image obtained by using the X-ray detector according to embodiments of the present disclosure is 227.45. FIG. 4A and FIG. 4B show a CT image obtained by using the photon counting detector and a CT image obtained by using the X-ray detector according to embodiments of the present disclosure, respectively.

As can be seen from the above description, with the X-ray detection method and the X-ray detector according to embodiments of the present disclosure, on one hand, signals for a plurality of energy windows can be obtained flexibly to improve the signal-to-noise ratio of the output signal; on the other hand, the number of output channels can be reduced and thus the bit rate of the output data can be reduced, which makes the X-ray detection method and the X-ray detector suitable for the spectral CT signal acquisition of higher efficiency. In addition, according to imaging requirements, weights can be easily adjusted to achieve a task-based signal acquisition optimization, such as discriminating scattered photons by an energy discriminator, proportionally reducing weights, thereby reducing or eliminating the effects of scattering.

The above described matrix obtaining unit may be implemented as hardware, software, firmware, or a combination thereof. When implemented in hardware, it can be, for example, an electronic circuit, an application specific integrated circuit (ASIC), suitable firmware, plug-ins, function cards, and the like. When implemented in software, elements of the present disclosure may be programs or code segments that are used to perform required tasks. The program or code segments can be stored in a machine readable medium or transmitted over a transmission medium or communication link through a data signal carried in a carrier. A "machine-readable medium" may include any medium that can store or transfer information. Examples of machine readable media include electronic circuits, semiconductor memory devices, ROM, flash memory, erasable ROM (EROM), floppy disks, CD-ROMs, optical disks, hard disks, fiber optic media, radio frequency (RF) links, and the like. The code segments can be downloaded via a computer network such as the Internet, an intranet, and the like.

The present disclosure may be embodied in other specific forms without departing from its spirit and essential characteristics. For example, the algorithms described in the specific embodiments can be modified, while the system architecture does not depart from the basic spirit of the present disclosure. Therefore, the present embodiments are to be considered in all respects as illustrative and not restrictive. The scope of the present disclosure is defined by the appended claims rather than the above description, and thus all modifications that come within the scope of the claims and equivalents thereof are included in the scope of the present disclosure.

What is claimed is:

1. An X-ray detection method, comprising:
receiving photons emitted by an X-ray source;
dividing an energy range of the photons emitted by the X-ray source into a number N of energy windows respectively corresponding to N energy window discriminators, where N is an integer greater than 0;
obtaining a weighting factor for each of the number N of energy windows based on linear attenuation coefficients of a substance of interest and a background substance of an imaging target;
obtaining a weighting factor matrix for M output channels of an X-ray detector based on the weighting factor for each of the number N of energy windows, where M is an integer greater than 0;
counting, via each of the N energy window discriminators, a number of photons that are emitted by the X-ray source and have an energy range falling into a respective energy window of the energy window discriminator; and
obtaining output results of the M output channels based on the weighting factor matrix and the counted numbers of photons having an energy range falling into individual energy windows of the number N of energy windows,
wherein for a k-th output channel of the M output channels, the X-ray detection method further comprises:
obtaining a weighting factor corresponding to an i-th energy window of the number N of energy windows and the k-th output channel in the weighting factor matrix by normalizing the weighting factor for the i-th energy window, when the i-th energy window belongs to the k-th output channel; and
setting the weighting factor corresponding to the i-th energy window and the k-th output channel in the weighting factor matrix to be 0, when the i-th energy window does not belong to the k-th output channel, where both i and k are integers greater than 0.

2. The X-ray detection method of claim 1, wherein the obtaining the output results of the M output channels comprises multiplying the weighting factor matrix by a column vector consisting of the numbers of photons having the energy range falling into the individual energy windows of the number N of energy windows.

3. The X-ray detection method of claim 1, wherein for an i-th energy window of the number N of energy windows, the X-ray detection method further comprises:
integrating the linear attenuation coefficient of the substance of interest and the linear attenuation coefficient of the background substance respectively within an energy range of the i-th energy window; and
calculating the weighting factor for the i-th energy window by carrying out an addition operation with an integration result of the linear attenuation coefficient of the substance of interest and an integration result of the linear attenuation coefficient of the background substance, where i is an integer greater than 0.

4. The X-ray detection method of claim 1, wherein for an i-th energy window of the number N of energy windows, the X-ray detection method further comprises:
calculating the weighting factor for the i-th energy window based on the linear attenuation coefficient of the substance of interest, the linear attenuation coefficient of the background substance, an energy spectrum of X-rays emitted by the X-ray source in the i-th energy window, an average thickness of the substance of interest penetrated by the X-rays emitted by the X-ray source, and an average thickness of the background substance penetrated by the X-rays emitted by the X-ray source, where i is an integer greater than 0.

5. An X-ray detector, comprising:
N energy window discriminators, each of which receives photons emitted by an X-ray source and counts a number of photons that are emitted by the X-ray source and have an energy range falling into a discrimination range of the energy window discriminator;
N sets of multipliers, each of which includes M multipliers, wherein a k-th multiplier in an i-th set of multipliers is configured to multiply the number of photons counted by an i-th energy window discriminator of the N energy window discriminators by a weighting factor at a k-th row and an i-th column of an M×N weighting factor matrix, where M, N, k and i are all integers greater than 0; and
M adders, wherein a k-th adder of the M adders is configured to accumulate products obtained at the k-th multipliers of individual sets of multipliers so as to obtain an output result of a k-th output channel of M output channels of the X-ray detector,
wherein the weighting factor matrix is obtained based on linear attenuation coefficients of a substance of interest and a background substance of an imaging target; and
the X-ray detector further comprises a matrix obtaining unit configured to obtain a weighting factor for each of N energy windows based on the linear attenuation coefficient of the substance of interest and the linear attenuation coefficient of the background substance, and obtain the weighting factor matrix based on the weighting factor for each of the N energy windows,
wherein the matrix obtaining unit is further configured to:
for the k-th output channel of the M output channels:
obtain a weighting factor corresponding to an i-th energy window of the N energy windows and the k-th output channel in the weighting factor matrix by normalizing the weighting factor for the i-th energy window, when the i-th energy window belongs to the k-th output channel; and
set the weighting factor corresponding to the i-th energy window and the k-th output channel in the weighting factor matrix to be 0, when the i-th energy window does not belong to the k-th output channel.

6. The X-ray detector of claim 5, wherein the matrix obtaining unit is further configured to:
for an i-th energy window of the N energy windows, integrate the linear attenuation coefficient of the substance of interest and the linear attenuation coefficient of the background substance respectively within an energy range of the i-th energy window; and
calculate the weighting factor for the i-th energy window by carrying out an addition operation with an integration result of the linear attenuation coefficient of the substance of interest and an integration result of the linear attenuation coefficient of the background substance.

7. The X-ray detector of claim 5, wherein the matrix obtaining unit is further configured to: for an i-th energy window of the N energy windows, calculate the weighting factor for the i-th energy window based on the linear attenuation coefficient of the substance of interest, the linear attenuation coefficient of the background substance, an energy spectrum of X-rays emitted by the X-ray source in the i-th energy window, an average thickness of the substance of interest penetrated by the X-rays emitted by the X-ray source, and an average thickness of the background substance penetrated by the X-rays emitted by the X-ray source, where i is an integer greater than 0.

* * * * *